(12) United States Patent
Hoshino

(10) Patent No.: US 10,545,103 B2
(45) Date of Patent: Jan. 28, 2020

(54) TALBOT IMAGING APPARATUS

(71) Applicant: KONICA MINOLTA, INC., Chiyoda-ku (JP)

(72) Inventor: Yoshihide Hoshino, Hachioji (JP)

(73) Assignee: Konica Minolta, Inc., Tokyo (JP)

( * ) Notice: Subject to any disclaimer, the term of this patent is extended or adjusted under 35 U.S.C. 154(b) by 211 days.

(21) Appl. No.: 15/606,280

(22) Filed: May 26, 2017

(65) Prior Publication Data

US 2017/0343494 A1 Nov. 30, 2017

(30) Foreign Application Priority Data

May 30, 2016 (JP) ................................ 2016-106892

(51) Int. Cl.
*G01N 23/20* (2018.01)
*A61B 6/00* (2006.01)

(52) U.S. Cl.
CPC ..... *G01N 23/20075* (2013.01); *A61B 6/4035* (2013.01); *A61B 6/484* (2013.01); *G01N 2223/401* (2013.01)

(58) Field of Classification Search
None
See application file for complete search history.

(56) References Cited

U.S. PATENT DOCUMENTS

| | | |
|---|---|---|
| 5,812,629 A | 9/1998 | Clauser et al. |
| 2011/0243300 A1* | 10/2011 | Kaneko ................. A61B 6/06 378/36 |
| 2011/0243302 A1 | 10/2011 | Murakoshi |
| 2012/0145912 A1 | 6/2012 | Iwakiri et al. |
| 2012/0236992 A1 | 9/2012 | Engel et al. |

(Continued)

FOREIGN PATENT DOCUMENTS

| | | |
|---|---|---|
| JP | 08-033621 | 2/1996 |
| JP | 08-241796 | 9/1996 |

(Continued)

OTHER PUBLICATIONS

Search Report dated Oct. 27, 2017 which issued in the corresponding European Patent Application No. 17172875.1.

(Continued)

*Primary Examiner* — Hoon K Song
(74) *Attorney, Agent, or Firm* — Cozen O'Connor (57) ABSTRACT

A Talbot imaging apparatus includes a radiation source, a plurality of gratings, a capturing control unit, a radiation detector, a setting unit and an irradiation control unit. The radiation source irradiates radiation. The capturing control unit relatively shifts the plurality of gratings and performs control of capturing a plurality of Moire images of a subject to generate a reconstructed image. The radiation detector acquires a captured Moire image. The setting unit sets a capturing condition for capturing a second and further Moire images by making a capturing result of a first Moire image be a reference, or sets a capturing condition for the plurality of Moire images by making another Moire image captured before capturing the plurality of Moire images be a reference. The irradiation control unit controls irradiation of radiation from the radiation source based on the capturing condition set by the setting unit.

9 Claims, 6 Drawing Sheets

(56) References Cited

U.S. PATENT DOCUMENTS

| | | | |
|---|---|---|---|
| 2014/0010344 A1* | 1/2014 | Nagatsuka | A61B 6/06 378/37 |
| 2014/0146945 A1 | 5/2014 | Fredenberg et al. | |
| 2015/0164459 A1 | 6/2015 | Ito | |
| 2015/0282780 A1 | 10/2015 | Hamano et al. | |

FOREIGN PATENT DOCUMENTS

| | | |
|---|---|---|
| JP | 2008-200361 | 9/2008 |
| JP | 2010-227432 | 10/2010 |
| JP | 2014-014379 | 1/2014 |
| JP | 2015-198765 | 11/2015 |
| WO | WO 2008/129939 | 10/2008 |
| WO | WO 2012/080914 | 6/2012 |

OTHER PUBLICATIONS

Junji Tanaka et al., "Cadaveric and in vivo human joint imaging based on differential phase contrast by X-ray Talbot-Lau interferometry", Z. Med. Phys. 23, pp. 222-227, 2012.

Examination Report dated Feb. 12, 2019 issued in European Patent Application No. 17172875.1.

Office Action dated Nov. 19, 2019 issued in Japanese Patent Application No. 2016-106892.

* cited by examiner

TALBOT IMAGING APPARATUS

BACKGROUND OF THE INVENTION

1. Field of the Invention

The present invention relates to an X-ray Talbot imaging apparatus which employs a Talbot interferometer or a Talbot-Lau interferometer.

2. Description of Related Art

An X-ray Talbot image capturing apparatus is known in which a Talbot interferometer or a Talbot-Lau interferometer, which captures and images the phase shift of X ray which occurs X ray is transmitted through a subject, and a radiation detector (Flat Panel Detector: FPD) are used (for example, refer to U.S. Pat. No. 5,812,629 and Junji Tanaka, et al. "Cadaveric and in vivo human joint imaging based on differential phase contrast by X-ray Talbot-Lau interferometry", Z. Med. Phys. 23(2012)222-227). Hereinafter, such an X-ray image capturing apparatus employing a Talbot interferometer, a Talbot-Lau interferometer or the like will be referred to as an X-ray Talbot imaging apparatus.

An X-ray Talbot imaging apparatus includes a first grating (G1 grating) and a second grating (G2 grating) which are provided with slits at regular intervals. The second grating is disposed at one of the positions where self images of the first grating are formed at regular intervals on downstream side of the first grating by irradiating X ray to the first grating from an X ray radiation source. A Moire fringe is formed on the second grating by disposing the second grating such that the extending direction of the slits of the second grating is slightly inclined relative to the extending direction of the slits of the first grating. The X-ray Talbot imaging apparatus is configured to detect and capture the image overlapped with this Moire fringe (hereinafter referred to as a Moire image) by an X-ray detector disposed on downstream side of the second grating.

When a subject is disposed between the radiation source (or the radiation source grating) and the first grating or between the first grating and the second grating, a distortion is formed on the Moire fringe by the subject. Therefore, when a plurality of Moire images are captured by an X-ray Talbot imaging apparatus while the first grating and the second grating are relatively shifted (fringe scanning method), an image such as a differential phase image, an absorption image and a small-angle scattering image can be reconstructed and formed by the image analysis of the Moire image in an image processing.

An X-ray imaging apparatus is also known which is configured to control the irradiation time of X ray to a subject by an automatic exposure control (AEC) in order to obtain an appropriate image by irradiating X ray of appropriate irradiation amount to the subject in X-ray imaging of the subject (for example, refer to JP H08-241796A).

SUMMARY OF THE INVENTION

The application of automatic exposure control described above may be adopted in an X-ray image capturing apparatus which employs a Talbot interferometer or a Talbot-Lau interferometer (X-ray Talbot imaging apparatus). However, even when a control is carried out such that the irradiation time of X ray merely becomes constant with respect to a subject in each capturing of a Moire image, incident amount of X ray to an X ray detector occurs dispersion depending on the position of a grating(s), and can affect image quality. As a result, the image analysis of Moire image in which Moire fringe is overlapped with an image of a subject is affected, and the reconstruction of an image such as a differential phase image, an absorption image and a small-scattering image becomes impossible to be properly carried out.

The present invention is made in consideration of the above problem. The object of the present invention is to provide a Talbot imaging apparatus which can properly capture a plurality of Moire images even when a plurality of gratings are relatively shifted, and thereby which can properly generate the reconstruction image.

To solve at least one of the objects described above, in accordance with one aspect of the present invention, there is provided a Talbot imaging apparatus including: a radiation source which irradiates radiation; a plurality of gratings; a capturing control unit which relatively shifts the plurality of gratings and which performs control of capturing a plurality of Moire images of a subject to generate a reconstructed image; a radiation detector which acquires a captured Moire image; a setting unit which sets a capturing condition for capturing a second and further Moire images by making a capturing result of a first Moire image be a reference, or which sets a capturing condition for the plurality of Moire images by making another Moire image captured before capturing the plurality of Moire images be a reference; and an irradiation control unit which controls irradiation of radiation from the radiation source based on the capturing condition set by the setting unit.

BRIEF DESCRIPTION OF THE DRAWINGS

The present invention will become more fully understood from the detailed description given hereinbelow and the appended drawings which are given byway of illustration only, and thus are not intended as a definition of the limits of the present invention, and wherein.

DESCRIPTION OF THE PREFERRED EMBODIMENTS

Hereinafter, embodiments of a Talbot imaging apparatus according to the present invention will be described with reference to drawings.

Figure 1:
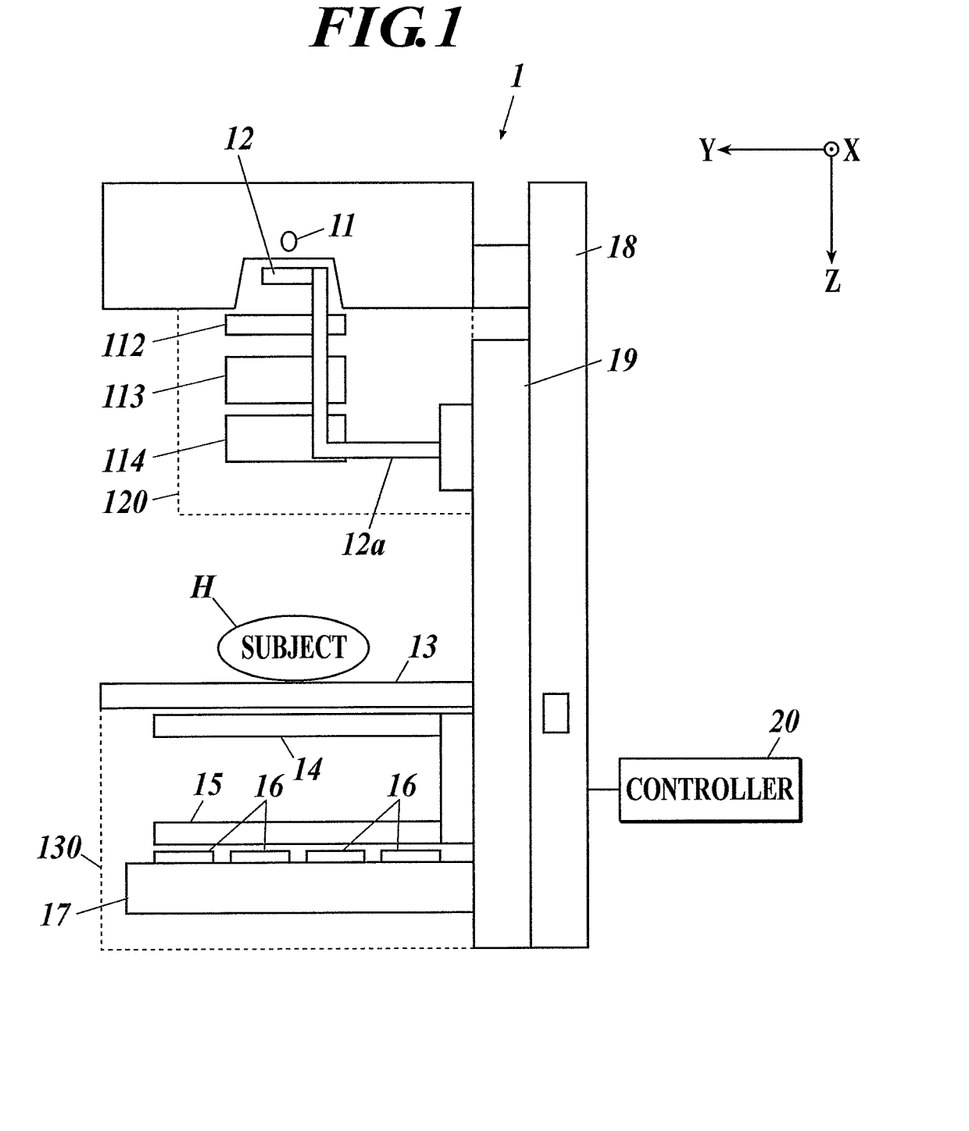
FIG. 1 is an overall view showing an X-ray Talbot imaging apparatus according to the present embodiment.

FIG. 1 is a view showing an overall configuration of an X-ray Talbot imaging apparatus 1 according to the present embodiment.

As shown in FIG. 1, the X-ray Talbot imaging apparatus 1 according to the present embodiment includes a radiation source 11, a radiation source grating 12, a subject table 13, a first grating 14, a second grating 15, a radiation dose detector 16, a radiation detector 17, a supporting post 18, a base 19 and a controller 20.

In the description below, the X-ray Talbot imaging apparatus 1 which captures an image using an X ray will be explained as an example. However, another radiation such as a neutron ray and a gamma ray may be used.

The principle common to a Talbot interferometer which is used in the X-ray Talbot imaging apparatus 1 and a Talbot-Lau interferometer will be explained with reference to FIG. 2.

Figure 2:
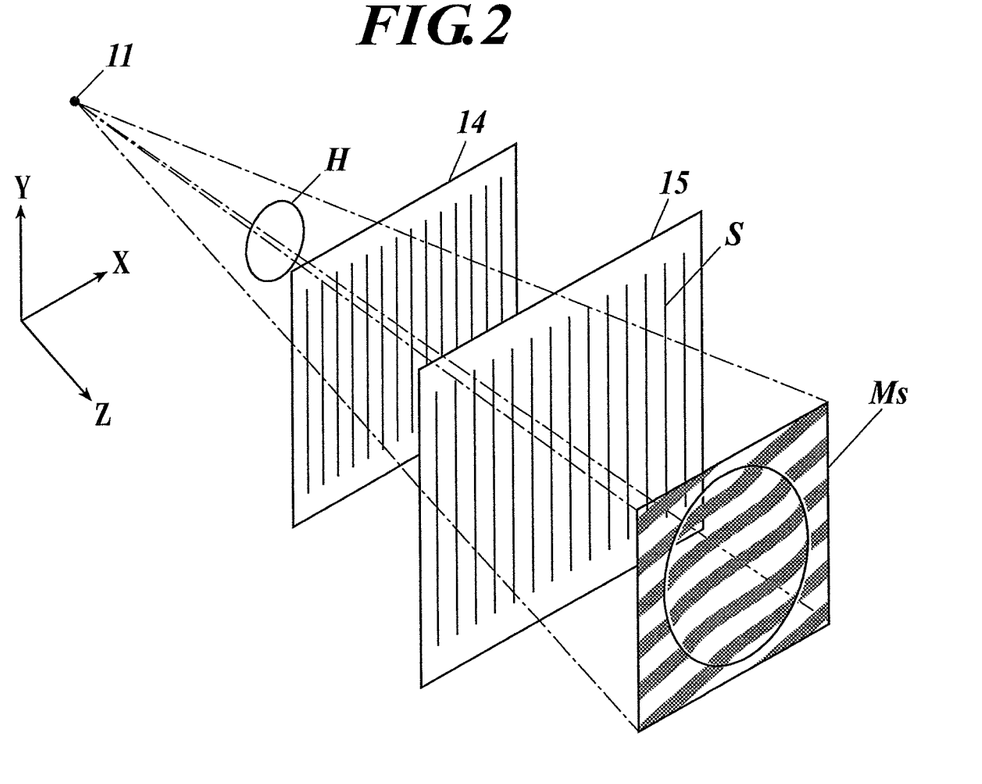
FIG. 2 is a view showing a principle of a Talbot interferometer and a Talbot-Lau interferometer.

Although FIG. 2 shows a Talbot interferometer, a Talbot-Lau interferometer is also explained in a basically similar manner. Also, the first grating 14 and the second grating 15 are formed from a single silicon wafer as an example. However, a configuration in which plural small gratings are arranged next to each other is similarly explained (not shown), for example.

In a Talbot ferrometer, the radiation source 11, the first grating 14 and the second grating 15 are arranged along the irradiation direction (z direction) of radiation in this order. Although an illustration is omitted, in the case of a Talbot-Lau interferometer, the radiation source grating 12 is arranged in proximity of the radiation source 11 (refer to FIG. 1, for example). As shown in FIG. 2, a Talbot interferometer and a Talbot-Lau interferometer are configured such that a subject H is arranged at a position upstream of the first grating 14 along the irradiation direction of the radiation. Although an illustration is omitted, a configuration in which the subject H is arranged at a position downstream of the first grating 14 along the irradiation direction of the radiation is also possible.

Figure 3:
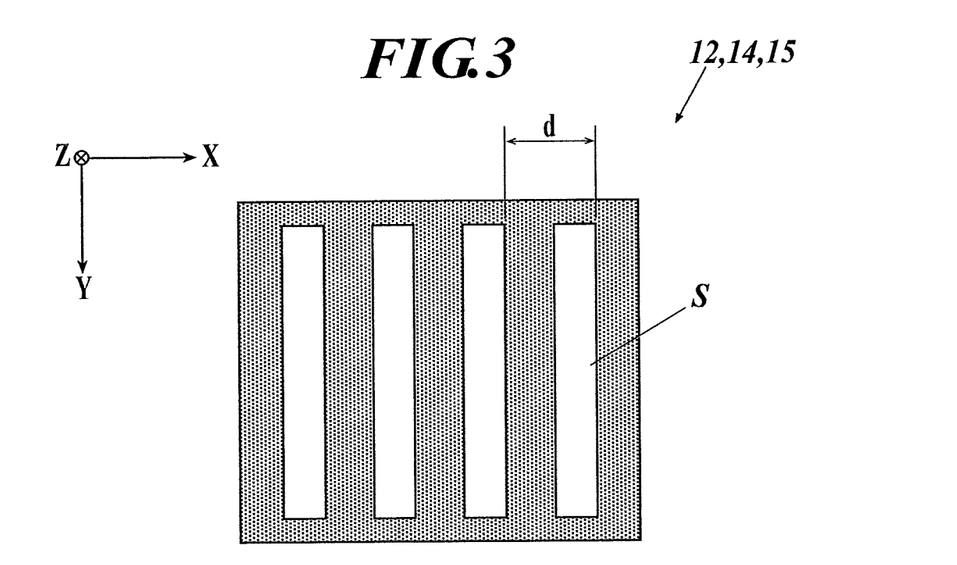
FIG. 3 is an explanatory view in which a grating is provided with a plurality of slits.

As shown in FIG. 3, a plurality of slits S are formed so as to be arranged at predetermined intervals d along x direction perpendicular to z direction which is the irradiation direction of the radiation in the first grating 14 and the second grating 15 (also in the radiation source grating 12 in the case of a Talbot-Lau interferometer). The predetermined intervals d are different in each of the first grating 14, the second grating 15 and the radiation source grating 12. In FIG. 3, the slits S are illustrated very largely relative to the grating for ease of comprehension.

When the radiation irradiated from the radiation source 11 (in the case of a Talbot-Lau interferometer, the radiation which is irradiated from the radiation source 11 and which is converted to the radiation from plural light sources at the radiation source grating 12) is transmitted through the first grating 14, the transmitted radiation forms images at regular intervals along z direction. These images are referred to as self images (also referred to as grating images, for example). The phenomenon in which the self images are formed at regular intervals along z direction in this manner is called Talbot effect.

As shown in FIG. 2, the second grating 15 is disposed at a position where the self image of the first grating 14 is formed. In this case, the second grating 15 is disposed such that the extending direction (y direction) of the slits S of the second grating 15 is slightly at an angle relative to the extending direction of the slits S of the first grating 14. By disposing the second grating 15 in such a manner, a Moire image Ms composed only of Moire fringes appears. In FIG. 2, if the Moire image Ms is shown on the second grating 15, the Moire fringes and the slits S are mixed and difficult to understand, and thus, the Moire image is shown spaced apart from the second grating 15. However, actually, the Moire image Ms is formed on the second grating 15 or on a downstream side thereof.

When the subject H exists in the range where the radiation is irradiated, the phase of the radiation is shifted due to the subject H. Thus, the Moire fringes of the Moire image Ms is disturbed such that a boundary is formed corresponding to edges of the subject. The Moire image Ms which is disturbed by the subject H on the second grating 15 or on the downstream side thereof as shown in FIG. 2.

Described above is the principle of a Talbot interferometer and a Talbot-Lau interferometer. The radiation detector 17 disposed downstream of the second grating 15 is configured to capture the Moire image Ms described above. In the present embodiment, the X-ray Talbot imaging apparatus 1 is configured in this way in accordance with the principle described above.

Hereinafter, the configuration of the X-ray Talbot imaging apparatus 1 according to the present embodiment will be explained.

In the present embodiment, the case where the X-ray Talbot imaging apparatus 1 is an X-ray Talbot imaging apparatus employing a Talbot-Lau interferometer which includes the radiation source grating 12 will be explained. However, an X-ray Talbot imaging apparatus employing a Talbot interferometer which does not include the radiation source grating 12 and which only includes the first grating 14 and the second grating 15 will be explained in a similar manner.

In the following, as shown in FIG. 1, the X-ray Talbot imaging apparatus 1 is configured such that the radiation source 11 disposed above irradiates radiation toward the subject below will be explained. The present invention is not limited to this case. The present invention may be configured such that the radiation source 11 irradiates radiation in the horizontal direction and any direction to capture the Moire image Ms of the subject.

The radiation source 11 includes, for example, a Coolidge X ray source or a rotating anode X ray source which is widely employed in a medical setting in general. However, the radiation source 11 may be configured so as to include a radiation source of the type other than these (a tube).

The radiation source grating 12 is disposed on the downstream side of the radiation source 11 along the irradiation direction (z direction) of radiation.

The radiation source grating 12 is not attached to the radiation source 11 in order that the vibration of the radiation source 11 may not propagate to the radiation source grating 12 or the like. The radiation source grating 12 is attached to the base 19 provided on the supporting post 18 via a fixing member 12a.

In addition to the radiation source grating 12, other elements are attached to the fixing member 12a, the other elements being an X-ray filter (additional filter) 112 to change the radiation quality of the radiation which is transmitted by the radiation source grating 12, an irradiated field diaphragm 113 to limit the irradiated field of radiation to be irradiated, an irradiated field lump 114 to carry out a position adjustment by irradiating visible light instead of radiation before irradiating radiation and the like. A first cover unit 120 is disposed around the radiation grating 12 and the like to protect them.

The subject table 13 on which the subject can be placed, the first grating 14, the second grating 15, the radiation dose detector 16, the radiation detector 17 and the like are provided on the downstream side of the radiation grating 12 along the irradiation direction (z direction) of radiation. The distance between the first grating 14 and the second grating 15 can be adjusted such that the second grating 15 is disposed at the position where one of self images formed at regular intervals along z direction from the first grating 14 by the radiation which is irradiated from the radiation source 11 and which is transmitted by the first grating 14 as described above.

The radiation detector 17 is disposed on the downstream side of the second grating 15 along the irradiation direction (z direction) of radiation. The radiation detector 17 is configured so as to capture the Moire image Ms formed on the second grating 15 as described above. As shown in FIG. 1, a second cover unit 130 is provided in order to protect the radiation detector 17 and the like from a patient's leg or the like which touches or bumps to the first grating 14, the second grating 15, the radiation detector 17 or the like.

Although an illustration is omitted, the radiation detector (FPD) 17 is configured such that conversion elements which generate electric signals in response to irradiated radiation are disposed in two dimensions (matrix-like) and such that the radiation detector 17 reads the electric signals generated by the conversion elements as image signals. The radiation detector 17 captures the Moire image Ms which is a radiation image formed on the second grating 15 as an image signal of each conversion element.

In case where the X-ray Talbot imaging apparatus 1 is configured so as to capture a plurality of Moire images Ms (for example, Moire images Ms1, Ms2, Ms3 and the like) with use of so called fringe scanning method (described below), a plurality of Moire images Ms are captured while the relative position of the first grating 14 and the second grating 15 is shifted in x direction shown in FIG. 1 and so on (that is, the direction perpendicular to the extending direction (y direction) of the slits S). Although an illustration is omitted, a moving device or the like is provided for shifting the relative position of the first grating 14 and the second grating 15 along x direction.

The radiation dose detector 16 which detects the radiation dose of X ray which is transmitted through the subject H is provided between the second grating 15 and the radiation detector 17. That is, the radiation dose detector 16 is arranged on the downstream side of the second grating 15 along the irradiation direction of radiation, and is arranged on the upstream side of the radiation detector 17 along the irradiation direction of radiation.

Figure 4:
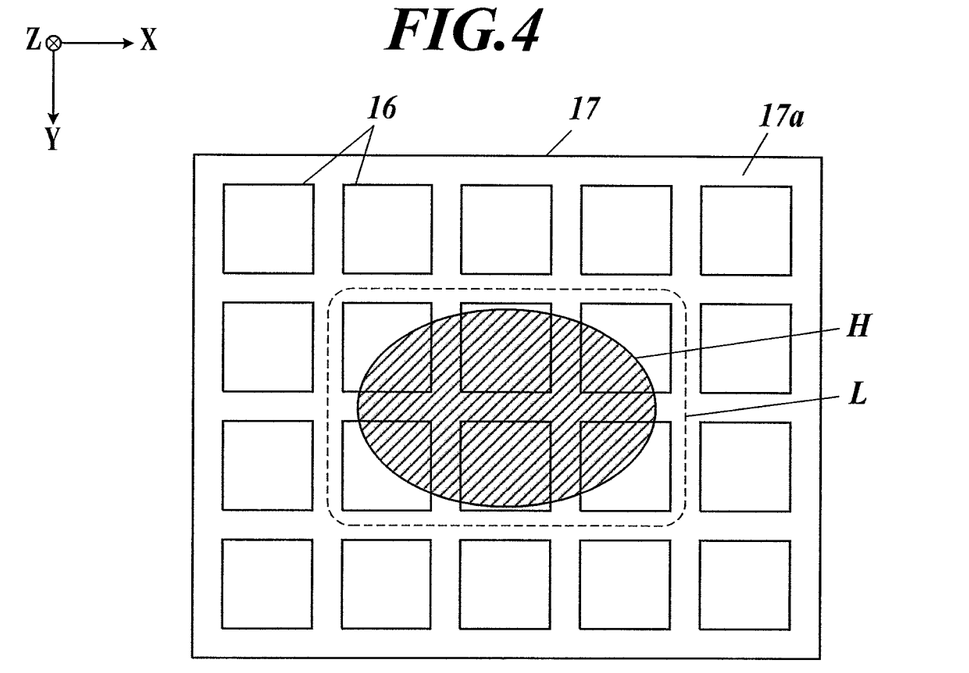
FIG. 4 is a schematic view showing a positional relationship between a radiation dose detector and a radiation detector.

The radiation dose detector 16 is formed of, for example, a resin film which transmits radiation. As shown in FIG. 4, a plurality of radiation dose detectors 16 is provided so as to be arranged on the substantially entire surface of the upstream side surface of the radiation detector 17 along irradiation direction of radiation (radiation incident surface) 17a.

That is, as described above, in the radiation detector 17, the conversion elements which generate electric signals in response to irradiated radiation are arranged in two dimensions, and a plurality of radiation dose detectors 16 are disposed on the substantially entire surface of the radiation incident surface 17a of the radiation detector 17 so as to correspond to the arrangement of the conversion elements. For example, in FIG. 4, five radiation dose detectors 16 are arranged along x direction, four radiation dose detectors 16 are arranged along y direction and twenty radiation dose detectors 16 are arranged in total.

Figure 7:
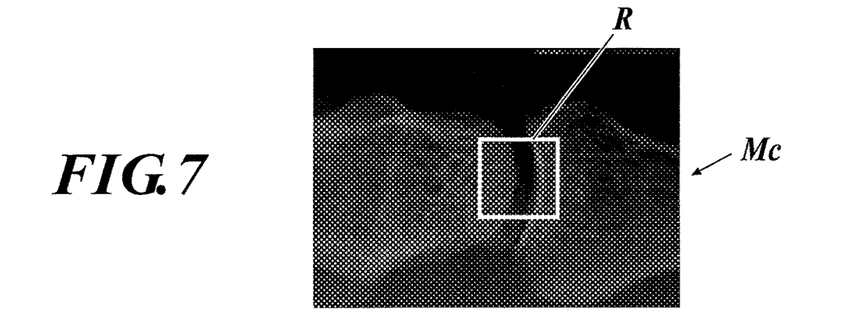
FIG. 7 is a view showing an example of a Moire image for confirmation.

Therefore, even when the conversion elements used for capturing an Moire image Ms is changed in accordance with the size of the subject H (shown by hatched lines in FIG. 4), the position and size of the region of interest R (see FIG. 7) or the like, the radiation dose detector(s) 16 which correspond(s) to the conversion elements used for capturing the Moire image Ms of the subject H (the radiation dose detectors 16 encircled by a dotted line L in FIG. 4) is specified among a plurality of radiation dose detectors 16, and the radiation dose of X ray falling onto the specified radiation dose detector 16 can be detected.

The arrangement and number of the radiation dose detector 16 is shown as an example, but is not limitative. For example, a single radiation dose detector 16 may be provided corresponding to a predetermined position (for example, the center position) of the radiation incident surface 17a of the radiation detector 17. In this case, since the radiation dose detector 16 which is used for setting the capturing condition is determined to one radiation dose detector 16, a determination unit (control unit 201) described below is not necessarily needed.

Next, the controller 20 will be explained with reference to FIG. 5.

Figure 5:
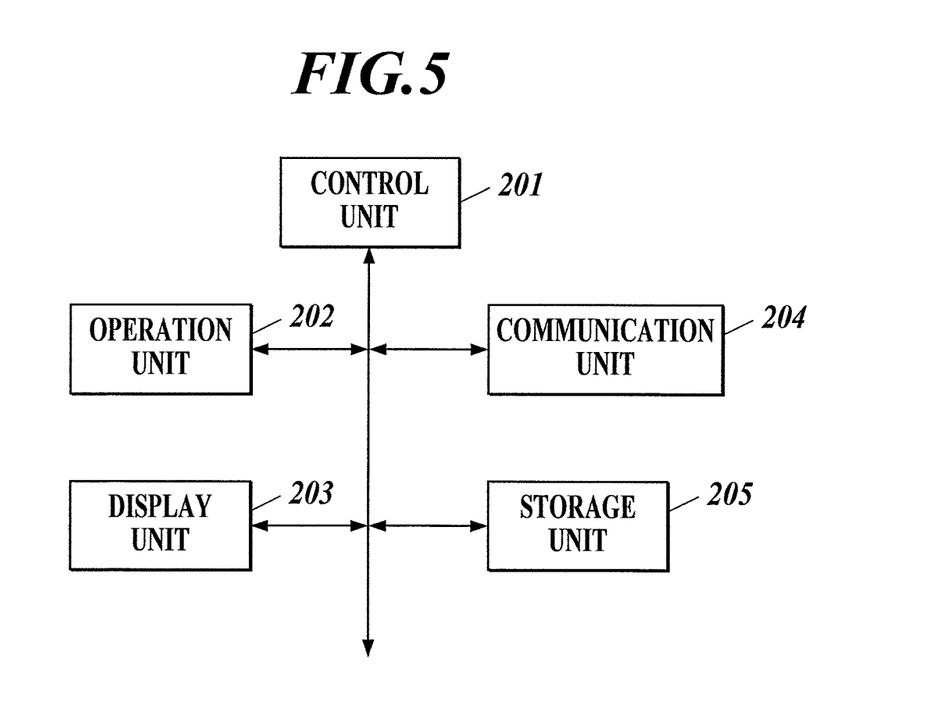
FIG. 5 is a block diagram showing functional configuration of a controller.

FIG. 5 is a block diagram showing functional configuration of the controller 20.

The controller 20 is constituted by a general-purpose computer, a specialized control device, or the like. In the specific, the controller 20 includes a control unit 201, an operation unit 202, a display unit 203, a communication unit 204 and a storage unit 205.

The control unit 201 is constituted by a central processing unit (CPU), a random access memory (RAM) or the like, and performs various processing in cooperation with a program stored in the storage unit 205. The control unit 201 is connected to each component such as the radiation source 11, the radiation dose detector 16 and the radiation detector 17. The control unit 201 performs radiation capturing control processing (described below) to control each component of the X-ray Talbot imaging apparatus 1.

For example, the control unit 201 is configured to perform the overall control of the X-ray Talbot imaging apparatus 1 such as the setting of a tube voltage, a tube current, an irradiation time and the like of the radiation source 11. Also, when the X-ray Talbot imaging apparatus 1 captures a plurality of Moire images Ms by fringe scanning method, the control unit 201 controls the moving device described above such that the first grating 14 (or the second grating 15 or both gratings) is controlled so as to be moved by every predetermined distance.

Figure 9A:
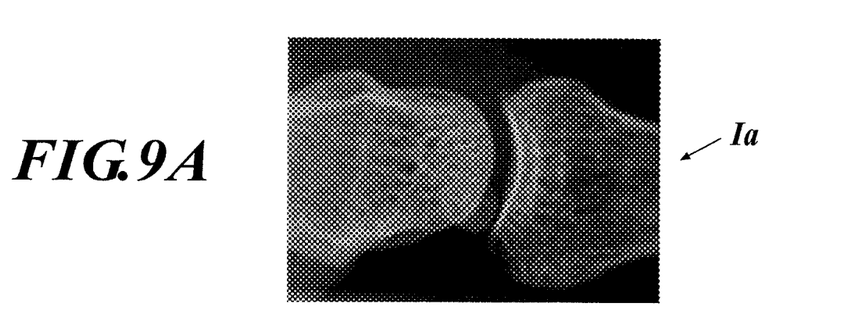
FIG. 9A is a view showing an example of an absorption image.
Figure 9B:
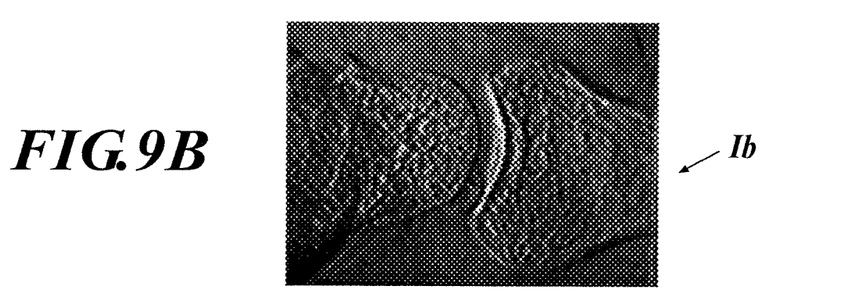
FIG. 9B is a view showing an example of a differential phase image.

Also, based on a plurality of Moire images Ms (for example, Moire images Ms1, Ms2, Ms3 and the like) sent from the radiation detector 17, the control unit 201 generates a reconstructed image such as an absorption image Ia (See FIG. 9A), a differential phase image Ib (see FIG. 9B), a small-angle scattering image (illustration omitted), or sends a plurality of Moire images Ms to an external image processing apparatus via the communication unit 204 to make the external image processing unit generate a reconstructed image such as an absorption image Ia, a differential phase image Ib and a small-angle scattering image.

The operation unit 202 includes an irradiation switch and a key group for operation inputting a capturing condition as well as a touch panel which is formed integrally with a display of the display unit 203, and outputs operation signals in response to an operation thereof to the control unit 201. The operation unit 202 may be used for designating the region of interest R of the subject H.

The display unit 203 displays, in accordance with the display control of the control unit 201, an operation screen, an operation state of the X-ray Talbot imaging apparatus 1 or the like on the display.

The communication unit 204 includes a communication interface and communicates with an external device on a network.

The storage unit 205 stores a program(s) to be executed by the control unit 201 and data necessary to execute the program(s). Also, the storage unit 205 stores a Moire image Ms obtained by the radiation detector 17.

The X-ray Talbot imaging apparatus 1 of the present embodiment captures a Moire image Ms necessary to generate a reconstructed image such as an absorption image Ia, a differential phase image Ib and a small-angle scattering image with use of fringe scanning method.

In fringe scanning, in general, among a plurality of gratings (the radiation source grating 12, the first grating 14 and the second grating 15), any one grating (for example, the second grating 15) or two gratings are relatively moved in periodic direction (x direction) of the slits S, and capturing is performed M times (M step capturing) (M>2 for an absorption image Ia, M>3 for a differential phase image Ib and a small-angle scattering image, where M is a positive integer) to obtain M Moire images Ms necessary to generate a reconstructed image. In a specific, for example, when the period of the slits of a grating to be moved is d (μm), moving the grating along the periodic direction of the slits by d/M (μm) and capturing an image are repeated to obtain M Moire images Ms. In such a case, the control unit 201 functions as a capturing control unit which relatively shifts a plurality of gratings and performs control of capturing a plurality of Moire images Ms of the subject to generate a reconstructed image.

When a plurality of Moire images are captured as described above, the control unit 201 performs radiation capturing control processing and functions as a setting unit, an irradiation control unit, an obtaining unit and the determination unit.

[Radiation Capturing Control Processing]

Hereinafter, the radiation capturing control processing performed by the X-ray Talbot imaging apparatus 1 will be explained in detail.

The control unit (the setting unit, the irradiation control unit) 201 sets a capturing condition for capturing a plurality of Moire images Ms (for example, Moire images Ms1, Ms2, Ms3 and the like; see FIGS. 8A to 8C) and controls the irradiation of X ray from the radiation source 11 based on the set capturing condition.

Specifically, the control unit 201 performs a first method or a second method. In the first method, among the capturing of a plurality of Moire images Ms, the capturing condition for capturing the second and further Moire images Ms2, Ms3 (see FIGS. 8B and 8C) is set with the capturing result of the first Moire image Ms1 (see FIG. 8A) being set as a reference. In the second method, the capturing condition for capturing a plurality of Moire images Ms is set with the capturing result of another Moire image captured before the plurality of Moire images Ms (for example, a Moire image Mc for confirmation (see FIG. 7) or a Moire image Mr captured without a subject (see FIG. 6A)) being as a reference.

The capturing condition may include the irradiation time, tube voltage and tube current of the radiation source 11 and the like. Other than these, the capturing condition may include the type of the X-ray filter (additional filter) used when a Moire image Ms is captured.

[First Method]

Setting of the capturing condition in the first method will be explained.

In this first method, the control unit 201 sets the capturing condition for capturing the second and further Moire images Ms by making the radiation dose of X ray which is detected by the radiation dose detector 16 when the first Moire image Ms is captured be as a reference. That is, in the fringe scanning method, the capturing of a Moire image is performed plural times while a plurality of gratings are being relatively shifted (for example, the relative position of the second grating 15 or the like is changed with respect to the first grating 14). Thus, even when a control is performed such that the radiation dose of X ray falling on the radiation dose detector 16 becomes constant, the radiation dose detector 16 detects the radiation dose in a state where Moire fringes are overlapped, and the radiation dose of the subject of the first capturing and the radiation dose of the subject of the second and further capturing are not possibly constant.

Therefore, when the first Moire image Ms1 is captured, the radiation dose of X ray falling on the radiation dose detector 16 is detected. The control unit 201 sets the capturing condition such as the irradiation time, tube voltage and tube current of the radiation source 11 for the capturing of the second and further Moire images Ms2, Ms3 and the like, regardless of the radiation dose of X ray detected by the radiation dose detector 16, based on the radiation dose of X ray which is detected when the first Moire image Ms1 is captured.

Specifically, the control unit 201 can perform an automatic exposure control in cooperation with the radiation dose detector 16, and sets the capturing condition for capturing the second and further Moire images Ms2, Ms3 and the like with use of the automatic exposure control.

In the automatic exposure control, basically, when the radiation dose of X ray falling on the radiation dose detector 16 becomes a predetermined value, the radiation dose detector 16 outputs an instruction signal indicating that the radiation dose of the incident X ray becomes a predetermined value to the control unit 201. When the instruction signal output from the radiation dose detector 16 is input to the control unit 201, the control unit 201 outputs a control signal for stopping the irradiation of X ray from the radiation source 11 to the radiation source 11 and stops the irradiation of X ray from the radiation source 11.

The radiation detector 16 detects the radiation dose of X ray which is incident when the first Moire image Ms1 is captured. With respect to the capturing of the second and further Moire images Ms2, Ms3 and the like, the control unit 201 sets the capturing condition for the second and further Moire images Ms2, Ms3 and the like such as the irradiation time, tube voltage and tube current of the radiation source 11 based on the radiation dose detected by the radiation dose detector 16 when the first Moire image Ms1 is captured.

The control unit 201 may set the capturing condition for capturing the first Moire image Ms1 such as the irradiation time of the radiation source 11 taking into account the intensity of the pixel value of a Moire image at the position corresponding to the radiation dose detector 16.

That is, before the capturing of a plurality of Moire images Ms (real capturing), a plurality of Moire images Mr without a subject are captured in a state where no subject H is placed on the subject table 3 (see FIG. 6A) or a Moire image Mc for confirmation is captured for confirming the capturing position of the subject H on the subject table 3 (scout capturing), for example.

The Moire image Mr without a subject is captured in a state where the relative position of a plurality of gratings (for example, the relative position of the second grating 15 with respect to the first grating 14) is the same as that of the real capturing. The Moire image Mr without a subject is used for generating an reconstructed image such as an absorption image Ia, a differential phase image Ib and a small-angle scattering image after the capturing of a plurality of Moire images Ms.

Figure 6A:
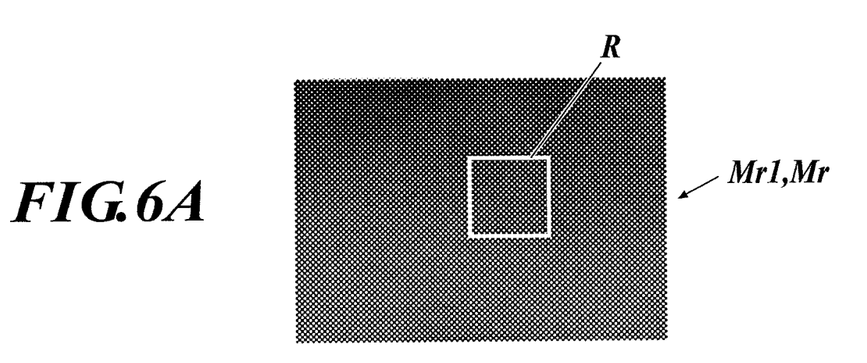
FIG. 6A is a view showing an example of a Moire image without a subject.
Figure 6B:
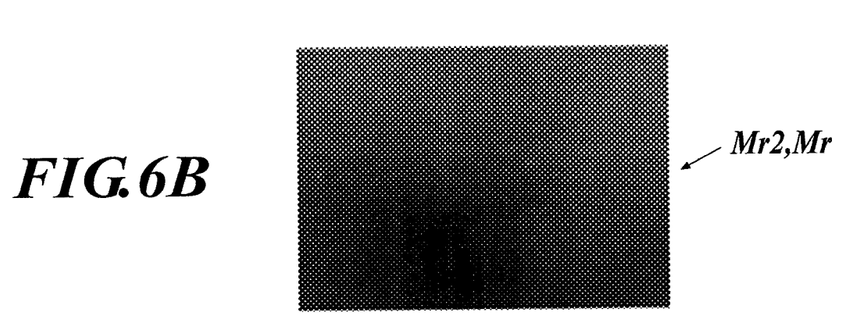
FIG. 6B is a view showing an example of a Moire image without a subject.
Figure 6C:
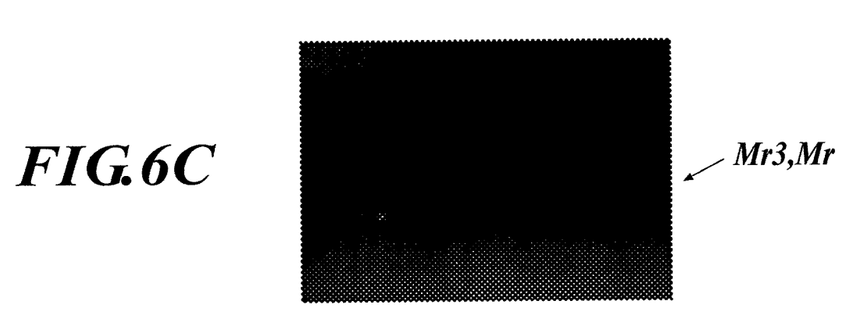
FIG. 6C is a view showing an example of a Moire image without a subject.
Figure 8A:
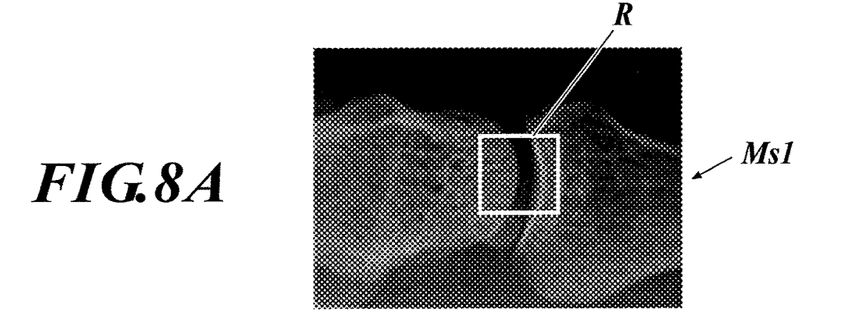
FIG. 8A is a view showing an example of a Moire image.
Figure 8B:
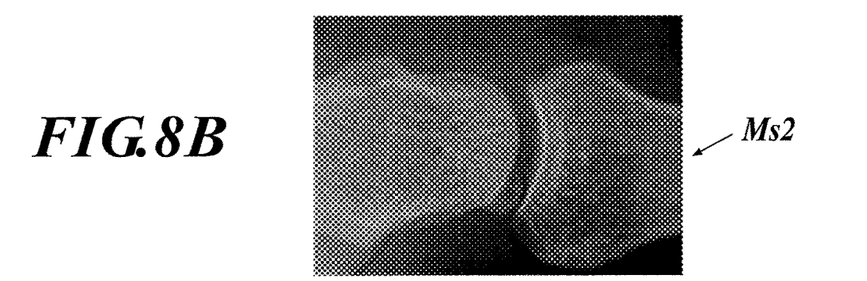
FIG. 8B is a view showing an example of a Moire image.
Figure 8C:
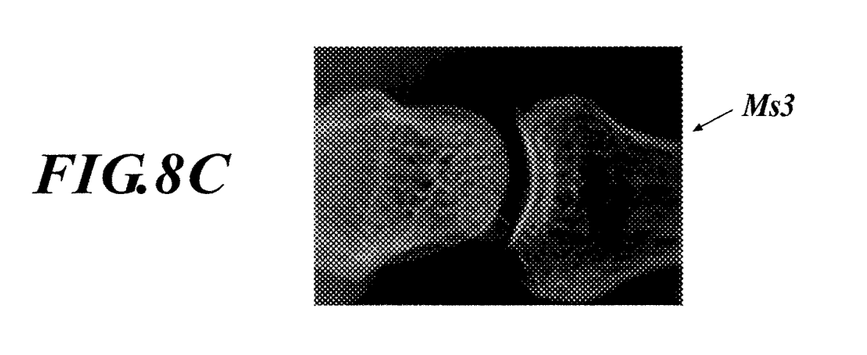
FIG. 8C is a view showing an example of a Moire image.

For example, the relative positions of a plurality of gratings are the same when the Moire image Mr1 without a subject shown in FIG. 6A and the Moire image Ms1 Shown in FIG. 8A are captured. Similarly, the relative positions of a plurality of gratings are the same when the Moire image Mr2 without a subject shown in FIG. 6B and the Moire image Ms2 shown in FIG. 8B are captured. The relative positions of a plurality of gratings are the same when the Moire image Mr3 without a subject shown in FIG. 6C and the Moire image Ms3 shown in FIG. 8C are captured.

Although a region of interest R is shown in the Moire image Mr1 without a subject shown in FIG. 6A, the region of interest R is not designated in the capturing of the Moire image Mr1 without a subject. For example, a position corresponding to the region of interest R designated in the Moire image Mc for confirmation is applied.

The Moire image Mc for confirmation is used for confirming the capturing position of a subject H on the subject table 13, and is used for the position adjustment of the subject H when the real capturing of a plurality of Moire images Ms are performed. The region of interest R of a subject H is set in the Moire image Mc for confirmation as described below.

The region of interest R of a subject H is a region which includes a diagnosis target such as a joint. The setting of the position and size of the region of interest R may be performed automatically based on the anatomical structure of a specific part of a human body which is a subject H, and may be designated by a user's operation on the operation unit 202.

The control unit (the acquisition unit) 201 acquires the intensity of a plurality of Moire images Mr without a subject (for example, an average value of pixel values). The control unit (the determination unit) 201 determines the radiation dose detector(s) 16 (the radiation dose detectors 16 encircled by a dotted line in FIG. 4) among a plurality of radiation dose detectors 16 by making, for example, the size and position of a subject H and the size and position of the region of interest H designated in the Moire image Mc for confirmation be a reference.

The control unit 201 sets the capturing condition for capturing the first Moire image Ms1 based on the intensity of the pixel values at the position corresponding to the determined radiation dose detector 16 in the acquired Moire image Mr without a subject. Specifically, the control unit 201 sets the capturing condition for capturing the first Moire image Ms1 by comparing the intensities of the pixel values at the position corresponding to the radiation dose detector 16 in a plurality of Moire images Mr (for example, by comparing the intensity of the pixel value of the first Moire image Mr1 (see FIG. 6A) without a subject and the intensity of the pixel value of the second Moire image Mr2 (see FIG. 6B) without a subject).

Also, the control unit 201 sets the capturing condition for capturing the first Moire image Ms1 by adjusting the capturing condition when the Moire image Mc for confirmation is captured by making the pixel value corresponding to the region of interest R of a subject H in the Moire image Mc for confirmation be an reference.

For example, when the pixel value of the entire Moire image Mr without a subject or the region of interest R of a subject H of the Moire image Mc for confirmation (when the region of interest is not set, the pixel value of the entire Moire image Mc for confirmation) is relatively small (underexposure), the control unit 201 sets the irradiation time of the radiation source 11 for capturing the first Moire image Ms1 such that it is longer than the irradiation time when the Moire image Mr without a subject or the Moire image Mc for confirmation is captured.

On the other hand, for example, when the pixel value of the entire Moire image Mr without a subject or the region of interest R of a subject H of the Moire image Mc for confirmation is relatively small (overexposure), the control unit 201 sets the irradiation time of the radiation source 11 for capturing the first Moire image Ms1 such that it is shorter than the irradiation time when the Moire image Mr without a subject or the Moire image Mc for confirmation is captured.

For example, when the control unit 201 is configured to change and set only the irradiation time of the radiation source 11 as the capturing condition in a state where the tube voltage and tube current of the radiation source 11 and the type of the X-ray filter 112 and the like are fixed in advance, the capturing condition for capturing the first Moire image Ms1 may be set taking into account the tube voltage and tube current of the radiation source 11 and the type of the X-ray filter 112. The control unit 201 also sets the capturing condition for capturing the second and further Moire images Ms2, Ms3 and the like by performing automatic exposure control based on the set capturing condition for capturing the first Moire image Ms1.

That is, the control unit 201 sets a capturing condition for capturing a Moire image Ms with at least one of the tube voltage and tube current of the radiation source 11 and the X-ray filter 112 of the radiation being as a reference.

[Second Method]

Next, setting of the capturing condition in the second method will be explained.

In the second method, it is not necessary for the radiation dose detector 16 to detect the radiation dose of X ray when a Moire image Ms is captured. That is, when the control unit 201 is configured to set the capturing condition for capturing a plurality of Moire images Ms by the second method, the X-ray Talbot imaging apparatus 1 does not necessarily need to include the radiation dose detector 16.

That is, the control unit 201 sets the capturing condition for performing the real capturing of a plurality of Moire images Ms (for example, irradiation time of the radiation source 11) by making the pixel value of a part corresponding to the region of interest R of a subject H in the Moire image Mc for confirmation captured before the capturing of the plurality of Moire images Ms (real capturing) be a reference. Specifically, after the Moire image Mc for confirmation is captured, the control unit 201 acquires, for example, the pixel value of the Moire image Mc for confirmation, and sets the capturing condition for capturing a plurality of Moire images Ms by correcting the capturing condition for capturing the Moire image Mc for confirmation in accordance with the pixel value of the part corresponding to the region of interest R of a subject H of the acquired Moire image Mc.

Figure 6D:
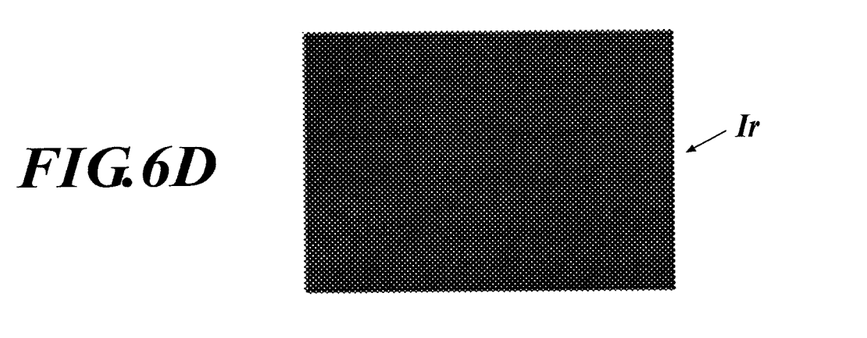
FIG. 6D is a view showing an example of an absorption image without a subject.

Also, the control unit 201 sets the capturing condition for performing the real capturing of a plurality of Moire images Ms (for example, irradiation time of the radiation source 11) by comparing the Moire image Mc for confirmation and the Moire image Mr without a subject which are captured before the plurality of Moire images Ms (real capturing). Specifically, after capturing a plurality of Moire images Mr without a subject (refer to FIGS. 6A, 6B and 6C), the control unit 201 reconstructs and generates an absorption image Ir without a subject (refer to FIG. 6D) based on the plurality of Moire images Mr without a subject. The control unit 201 sets the capturing condition for capturing a plurality of Moire images Ms by comparing the pixel values of the generated absorption image Ir and the pixel values of the Moire image Mc for confirmation. In this case, the control unit 201 may set the capturing condition for capturing a plurality of Moire images Ms by correcting the capturing condition with which the Moire image Mr without a subject or the Moire image Mc for confirmation is captured.

Similarly to the first method described above, even when the control unit 201 is configured to change and set only the irradiation time of the radiation source 11 as the capturing condition in a state where, for example, the tube voltage and tube current of the radiation source 11, the type of the X-ray filter 112 and the like are fixed in advance, the control unit 201 may set the capturing condition for capturing a Moire image Ms with at least one of the tube voltage and tube current of the radiation source 11 and the X-ray filter 112 of radiation being as a reference.

That is, the control unit 201 may set the capturing condition for capturing a plurality of Moire images Ms taking into account the tube voltage and tube current of the radiation source 11 and the type of X-ray filter 112 and the like.

As described above, according to the X-ray Talbot imaging apparatus 1 of the present embodiment, even when a plurality of gratings are relatively shifted, it is possible to capture a plurality of Moire images properly without being affected by the thickness of a subject and without causing dispersion of radiation dose of X ray to the radiation detector 17 when each of Moire images is captured. Therefore, it becomes possible to properly generate a reconstructed image such as an absorption image Ia, a differential phase image Ib and a small-angle scattering image.

Also, by making the X ray dose detected by the radiation dose detector 16 when the first Moire image Ms1 is captured be a reference, the capturing condition for capturing the second and further Moire images Ms2, Ms3 and the like can be properly set and the capturing a plurality of Moire images Ms for generating a reconstructed image can be properly performed.

Also, as to the capturing of the first Moire image Ms1, by correcting the capturing condition for capturing the Moire image Mr without a subject based on the intensity of the pixel value at the position corresponding to the radiation dose detector 16 when the Moire image Mr without a subject is captured, the capturing condition for capturing the first Moire image Ms1 can be properly set. In particular, by comparing the intensities of the pixel values at the positions corresponding to the radiation dose detector 16 in a plurality of Moire images Mr without a subject with each other, the capturing condition for capturing the first Moire image Ms1 can be more properly set.

Furthermore, by making the pixel value of a part corresponding to the region of interest R of a subject H in a Moire image Mc for confirmation, even in a case where a diagnostic target is a small joint, in case where X ray transmittances of a bone and a joint cavity are largely different from each other or the like, the capturing condition for capturing the first Moire image Ms1 can be properly set by correcting the capturing condition for capturing a Moire image Mc for confirmation.

Therefore, a capturing under a proper capturing condition is possible from the capturing of the first Moire image Ms1, and a plurality of Moire images Ms for generating a reconstructed image can be captured properly.

Also, by making the pixel value of a part corresponding to a region of interest R of a subject H in a Moire image Mc for confirmation which is captured before the capturing of a plurality of Moire images Ms be a reference, the capturing condition for capturing a plurality of Moire image Ms can be properly set by correcting the capturing condition for capturing a Moire image Mc for confirmation in accordance with the pixel value of the part corresponding to the region of interest R of the subject H in the Moire image Mc for confirmation. In this case, by comparing a Moire image Mr without a subject and a Moire image Mc for confirmation which are captured before the capturing of a plurality of Moire images Ms, the capturing condition for capturing a plurality of Moire image Ms can be more properly set.

Therefore, a plurality of Moire images Ms for generating a reconstructed image can be properly captured even if an automatic exposure control is not carried out by making the radiation dose of X ray to the radiation detector 17 (i.e., the dose of X ray detected by the radiation dose detector 16) be a reference.

Even when X rays of different radiation quality is used for the capturing of a Moire image Ms by changing the tube voltage and tube current of the radiation source 11, the type of the X-ray filter 112 or the like, the capturing condition for capturing the Moire image Ms can be properly set.

In the embodiment described above, the control unit 201 of the controller 20 of the X-ray Talbot imaging apparatus 1 is configured to function as a capturing control unit, a setting unit, an irradiation control unit, an acquisition unit and a determination unit. However, it is a mere example and is not limitative. For example, the X-ray Talbot imaging apparatus 1 itself may include an arithmetic device which has substantially the same function as that of the control unit 201 of the controller 20, and this arithmetic device may be configured to function as a capturing control unit, a setting unit, an irradiation control unit, an acquisition unit and a determination unit.

In addition, the present invention is not limited to the embodiment described above, and may be modified as needed without departing from the scope of the present invention.

The present patent application is based on Japanese Patent Application No 2016-106892 filed on May 30, 2016 with the Japan Patent Office and the entire description of the present patent application is disclosed in Japanese Patent Application No 2016-106892.

What is claimed is:

1. A Talbot imaging apparatus comprising:
   a radiation source which irradiates radiation;
   a plurality of gratings;
   a capturing control unit which relatively shifts the plurality of gratings and which performs control of capturing a plurality of Moire images of a subject to generate a reconstructed image;
   a radiation detector which acquires a captured Moire image;
   a setting unit which sets a capturing condition for capturing a second and further Moire images by making a capturing result of a first Moire image be a reference, or which sets a capturing condition for the plurality of Moire images by making another Moire image captured before capturing the plurality of Moire images be a reference; and an irradiation control unit which controls irradiation of radiation from the radiation source based on the capturing condition set by the setting unit.

2. The Talbot imaging apparatus according to claim 1, further comprising a radiation dose detector which detects radiation dose of radiation transmitted through a subject, wherein the setting unit sets the capturing condition for capturing the second and further Moire images by making the radiation dose of radiation detected by the radiation dose detector when the first Moire image is captured.

3. The Talbot imaging apparatus according to claim 1, wherein the radiation detector further acquires a Moire image without a subject which is captured in a state where a subject is not placed before capturing the plurality of Moire images, the Talbot imaging apparatus further comprises an acquisition unit which acquires an intensity of a pixel value of the Moire image without a subject, and the setting unit sets the capturing condition for capturing a Moire image based on an intensity of the pixel value of the Moire image without a subject at a position corresponding to the radiation detector, the intensity being acquired by the acquisition unit.

4. The Talbot imaging apparatus according to claim 3, wherein the radiation detector acquires a plurality of Moire images without an subject, and the setting unit sets the capturing condition for capturing a Moire image by comparing intensities of pixel values of the plurality of Moire images without a subject at positions corresponding to the radiation detector acquired by the acquisition unit.

5. The Talbot imaging apparatus according to claim 2, wherein a plurality of the radiation dose detectors are disposed on upstream side of the radiation detector along irradiation direction of radiation, the radiation detector further acquires a Moire image for confirmation captured before capturing the plurality of Moire images for confirming a capturing position of a subject, and the Talbot imaging apparatus further comprises a determination unit which determines a radiation dose detector, which is used when the setting unit sets the capturing condition, among the plurality of radiation dose detectors by making a region of interest of a subject in the Moire image for confirmation be a reference.

6. The Talbot imaging apparatus according to claim 1, wherein the radiation detector further acquires a Moire image for confirmation captured before capturing the plurality of Moire images for confirming a capturing position of a subject, and the setting unit sets the capturing condition for capturing a Moire image by making a pixel value of a part corresponding to a region of interest of a subject in the Moire image for confirmation be a reference.

7. The Talbot imaging apparatus according to claim 1, wherein the radiation detector further acquires a Moire image for confirmation as the another Moire image which is captured before capturing the plurality of Moire images for confirming a capturing position of a subject, and the setting unit sets the capturing condition for capturing the plurality of Moire images by making a pixel value of a part corresponding to a region of interest of a subject in the Moire image for confirmation be a reference.

8. The Talbot imaging apparatus according to claim 7, wherein the radiation detector further acquires a Moire image without a subject as the another Moire image which is captured before capturing the plurality of Moire images in a state where a subject is not placed, and the setting unit sets the capturing condition for capturing the plurality of Moire images by comparing the Moire image for confirmation and the Moire image without a subject.

9. The Talbot imaging apparatus according to claim 1, wherein the setting unit sets the capturing condition for capturing a Moire image by making at least one of a tube voltage and a tube current of the radiation source and a radiation filter be a reference.

* * * * *